(12) United States Patent
Albuquerque et al.

(10) Patent No.: US 9,983,105 B2
(45) Date of Patent: May 29, 2018

(54) LIQUID REAGENT STORAGE AND OPERATION OF ANALYTICAL DEVICES

(71) Applicant: BIOSURFIT, S.A., Aveiro (PT)

(72) Inventors: Carlota Albuquerque, Lisboa (PT); Tânia Tenreiro, Lisboa (PT); Nuno Reis, Lisboa (PT); João Garcia Da Fonseca, Lisboa (PT); Ricardo Marques Caleiro Cabeça, Lisboa (PT)

(73) Assignee: Biosurfit, S.A., Aveiro (PT)

( * ) Notice: Subject to any disclaimer, the term of this patent is extended or adjusted under 35 U.S.C. 154(b) by 0 days. days.

(21) Appl. No.: 15/630,578

(22) Filed: Jun. 22, 2017

(65) Prior Publication Data
US 2017/0282179 A1 Oct. 5, 2017

Related U.S. Application Data

(63) Continuation of application No. 15/584,719, filed on May 2, 2017, which is a continuation of application
(Continued)

(30) Foreign Application Priority Data

Apr. 2, 2011 (PT) .......................................... 105607

(51) Int. Cl.
*G01N 1/28* (2006.01)
*B01L 3/00* (2006.01)

(52) U.S. Cl.
CPC .......... *G01N 1/28* (2013.01); *B01L 3/502738* (2013.01); *B01L 3/502715* (2013.01);
(Continued)

(58) Field of Classification Search
CPC ....................................................... G01N 1/28
(Continued)

(56) References Cited

U.S. PATENT DOCUMENTS 5,457,053 A 10/1995 Burd
6,193,471 B1 * 2/2001 Paul .................... B01F 11/0071
417/118

(Continued)

FOREIGN PATENT DOCUMENTS

JP 2007-198949 8/2007
JP 2009-002933 1/2009
(Continued)

OTHER PUBLICATIONS

English translated Japanese Office Action to Japanese Application No. 2014-501804 dated Dec. 25, 2015.
(Continued)

*Primary Examiner* — Christopher Adam Hixson
*Assistant Examiner* — Emily R. Berkeley
(74) *Attorney, Agent, or Firm* — Brian L. Stender; Patterson Thuente Pedersen, P.A.

(57) ABSTRACT

Improved mechanisms for storing and introducing liquid volumes in a liquid handling device and, in particular, improved mechanisms for rupturing a liquid storage package to introduce liquid into the device, improvements to the stability of a liquid receiving chamber inside the device and improvements to liquid handling in the receiving chamber are achieved.

14 Claims, 5 Drawing Sheets

Related U.S. Application Data

No. 14/009,433, filed as application No. PCT/IB2012/051591 on Apr. 2, 2012, now Pat. No. 9,651,460.

(52) U.S. Cl.
CPC ....... *B01L 3/523* (2013.01); *B01L 2200/0642* (2013.01); *B01L 2200/0689* (2013.01); *B01L 2200/16* (2013.01); *B01L 2300/0806* (2013.01); *B01L 2300/087* (2013.01); *B01L 2300/123* (2013.01); *B01L 2400/0409* (2013.01); *B01L 2400/0481* (2013.01); *B01L 2400/0638* (2013.01); *B01L 2400/0683* (2013.01); *B01L 2400/086* (2013.01); *Y10T 436/2575* (2015.01)

(58) Field of Classification Search
USPC ........................................................ 422/502
See application file for complete search history.

(56) References Cited

U.S. PATENT DOCUMENTS

| | | | | |
|---|---|---|---|---|
| 8,096,314 B2* | 1/2012 | Mark | ................. | B01L 3/50273 137/1 |
| 2002/0123059 A1 | 9/2002 | Ho | | |
| 2005/0178218 A1 | 8/2005 | Montagu | | |
| 2006/0160243 A1* | 7/2006 | Tang | ........................ | G01N 1/40 436/177 |
| 2006/0183216 A1* | 8/2006 | Handique | ......... | B01L 3/502738 435/287.1 |
| 2008/0305006 A1* | 12/2008 | Cho | .................... | B01L 3/50273 422/68.1 |
| 2010/0009431 A1 | 1/2010 | Cho et al. | | |
| 2010/0021347 A1 | 1/2010 | Garcia Da Fonseca | | |

FOREIGN PATENT DOCUMENTS

| | | |
|---|---|---|
| JP | 2010-025776 | 2/2010 |
| WO | WO 2008/057000 A1 | 5/2008 |
| WO | WO 2010/077159 A1 | 7/2010 |
| WO | WO 2010/084190 A1 | 7/2010 |
| WO | WO 2011/003689 A1 | 1/2011 |

OTHER PUBLICATIONS

Application and File History for U.S. Appl. No. 14/009,433, filed Dec. 9, 2013. Inventors: Carlota Albuquerque et al.
Application and File History for U.S. Appl. No. 15/584,719, filed May 2, 2017. Inventors: Carlota Albuquerque et al.

* cited by examiner

LIQUID REAGENT STORAGE AND OPERATION OF ANALYTICAL DEVICES

CROSS-REFERENCE TO RELATED APPLICATIONS

This application is a continuation of application Ser. No. 15/584,719, filed May 2, 2017, which in turn is a continuation of application Ser. No. 14/009,433, filed Dec. 9, 2013, now U.S. Pat. No. 9,651,460, issued May 16, 2017, which is a National Phase entry of PCT Application No. PCT/IB2012/051591, filed Apr. 2, 2012, which claims priority from Portugal Application No. 105607, filed Apr. 2, 2011, each of which is hereby fully incorporated herein by reference.

TECHNICAL FIELD

The present invention relates to a device for storing and handling liquid and a method for introducing stored liquid into the device, for example using liquid storage containers such as blister packs. In particular, although not exclusively, the present invention relates to centrifugal microfluidic devices.

BACKGROUND

There are many circumstances where systems for performing analytical procedures involve equipment, such as an analyzer, designed to read disposable cartridges. Known systems and devices performing analytical procedures involving liquids contain liquid reagents handled by the analyzer. In many cases it is preferable to have analyzers without liquid handling functions to reduce cost, complexity and maintenance. Consequently, it is desirable to include liquid storage capabilities in the disposable cartridges.

Several types of analytical systems have been developed in the past, using disk-type cartridges, such as those described in WO2008057000. Different implementations have been developed to store liquids in storage receptacles on cartridges and then open those storage receptacles when the analysis is to be performed. One of these implementations in described in U.S. Pat. No. 5,457,053. Other implementations make use of active elements for opening the liquid storage receptacles, namely by action of optical radiation. One of these implementations is described in WO2010084190.

All of these implementations have significant limitations due to their intrinsic complexity, either in their production processes or in their required level of user interaction.

SUMMARY

Aspects of the invention are defined in the independent claims. Further, optional, features are defined in the dependent claims.

In some embodiments, there is provided a device for handling liquid comprising a body defining an internal liquid handling structure. The body defines a first aperture in an external surface of the body to provide an inlet port to the liquid handling structure. A bonding layer is secured to the external surface and defines a second aperture partially overlapping with the first aperture. As a result, the external surface is exposed on the first side of the first aperture and the bonding layer partially covers the first aperture on a second side, opposed to the first side. A liquid storage arrangement is secured to the bonding layer overlapping the first aperture to dispense liquid through the first aperture when a pressure exceeding a threshold pressure is applied to the liquid storage arrangement.

The material properties of the liquid storage arrangement, bonding layer and external surface may be selected such that the liquid storage arrangement reproducibly ruptures in the region of the first side of the first aperture in response to pressure exceeding the threshold pressure being applied to the liquid storage arrangement.

Advantageously, by disposing the bonding layer between the liquid storage arrangement and the external surface such that the external surface is exposed on one side and covered by the bonding layer on the other side, rupturing of the liquid storage arrangement in a reproducible fashion against the external surface where it is exposed is facilitated. At the same time, the overlap of the bonding layer with the first aperture provides a cushion against undesired rupturing in that region.

In some embodiments, there is provided a device for handling liquid comprising a body defining an internal liquid handling structure. The body defines a first aperture in an external surface to provide an inlet port to the liquid handling structure. A liquid storage arrangement is secured to the external surface to dispense liquid through the first aperture when a pressure exceeding a threshold pressure is applied to the liquid storage arrangement. The first aperture defines a sharp edge level with the external surface to facilitate rupturing the liquid storage arrangement.

Advantageously, by providing the first aperture with a sharp edge that is level with the external surface, manufacturing of the device is facilitated. For example, the first aperture (and edge) can be defined simply by an aperture process, for example by stamping. In some embodiments, the sharp edge includes a spike extending into the aperture, the spike being level with the external surface. The presence of the spike further helps to rupture the liquid storage arrangement reproducibly.

In some embodiments, a device for handling liquid comprises a body defining an internal liquid handling structure. The body defines a first aperture in an external surface to provide an inlet port to the liquid handling structure. A liquid storage arrangement is secured to the external surface to rupture and dispense liquid through the first aperture when a pressure exceeding a threshold pressure is applied to the liquid storage arrangement. The liquid handling structure comprises a liquid receiving chamber for receiving liquid from the liquid storage arrangement through the first aperture, when the liquid storage arrangement is ruptured. To prevent or reduce liquid ingress into a liquid outlet, vent port, or both, of the liquid receiving chamber, due to rupturing of the liquid storage arrangement, a flow resisting arrangement is disposed within the liquid receiving chamber between the first aperture and the liquid outlet, vent port, or both.

Advantageously, the flow resisting arrangement substantially holds the liquid away from the outlet and/or vent port until operation of the device begins, in spite of the introduction of liquid into the liquid receiving chamber from the liquid storage arrangement under high pressure when the liquid storage arrangement ruptures. To this end, the flow resisting arrangement may comprise one or more structural features disposed in the liquid receiving chamber to increase flow resistance to the liquid and/or provide surface potential energy barriers retaining the liquid away from the vent port and/or outlet.

In some embodiments, the flow resistance arrangement comprises a support structure disposed within the liquid receiving chamber to increase the structural strength of a wall between the external surface and a liquid receiving chamber. Other embodiments instead use a support structure which does not also have a flow resisting function. The support structure may comprise at least one column extending between the wall and an exposed surface of the liquid receiving chamber and, in some embodiments, may comprise an array of columns. In one particular form, the array of columns may be arranged as spaced rows of spaced columns in each row. In this form, each row provides a flow resisting arrangement, increasing resistance to flow by a reduction in flow cross section and also providing surface tension barriers to a liquid front passing each row. Other arrangements may be used to similar effect, for example using support and/or flow resisting structures which comprise one or more walls traversing the liquid receiving chamber and having orifices to enable liquid passage therethrough.

Further embodiments include the combination of the embodiments described above, for example combining the arrangements in relation to the liquid storage arrangement and its disposition for reproducible rupturing with the flow resisting and/or structural integrity enhancing features inside the liquid receiving chamber.

In some embodiments, the liquid storage arrangement may comprise a blister pack. In some particular embodiments, the liquid storage arrangement comprises a foil secured to the external surface and a cover secured to the foil to define a liquid holding chamber between the cover and the foil. In embodiments where a bonding layer is provided between the liquid storage arrangement and the external surface, the foil may be secured to the bonding layer.

In some embodiments, the device is arranged for liquid flow being driven through the liquid handling structure by virtue of a centrifugal force as the device is rotated about an axis of rotation. In some such centrifugal embodiments, the liquid handling structure comprises a liquid receiving chamber for receiving liquid from the first aperture and having an outlet port connected to an outlet conduit extending from the outlet port. The outlet conduit extends radially inward from the outlet port to a bend and radially outward from the bend, the bend being radially outside a fill level of the liquid receiving chamber.

Advantageously, this arrangement ensures that liquid is only dispensed under rotation from the liquid handling structure if a threshold level corresponding to the radial position of the bend is crossed by the liquid, thus ensuring that liquid is only dispensed if a minimum level is reached. In alternative embodiments, the bend is located radially inside of the fill level of the liquid receiving chamber. In such embodiments, liquid is retained in the liquid handling structure under initial rotation until the device is slowed down sufficiently for the liquid to be drawn into the outlet conduit by capillary forces to a sufficient advance such that the outlet subsequently acts as a siphon to empty the liquid handling structure during rotation (an arrangement typically referred to as "capillary siphon").

In some embodiments, the liquid receiving chamber has a radially outward aspect at the first aperture, which is radially inward of a radially outward aspect of the liquid receiving chamber at an opposed end, opposed to the first aperture. For example, the radially outward aspect may follow a spiral locus from an end adjacent the first aperture to the opposed end. This arrangement ensures that all liquid in the liquid receiving chamber is driven towards the opposed end by rotation, thus enabling it to flow through an outlet port disposed at that end to downstream liquid handling structures.

In some embodiments, the first aperture is being arranged to facilitate rupturing of the liquid storage arrangement at a location such that liquid inside the liquid storage arrangement to be dispensed during rotation of the device is radially inward of the location. For example, the sharp edge discussed above may be disposed at a radially outward aspect of the first aperture and/or the overlapping bonding layer region may be disposed at a radially inward aspect of the first aperture. This arrangement ensures efficient emptying of the liquid storage arrangement. In one particular embodiment, where the first aperture is arranged such that the location is substantially at a radially outermost aspect of the first aperture, substantially all of the liquid in the liquid storage arrangement can be emptied by rotation. For example, to this end, the sharp edge and/or spike discussed above may be disposed at a radially outermost aspect of the first aperture and/or the overlap of the bonding layer may be disposed at a radially innermost aspect of the first aperture.

In one embodiment, there is provided a method of introducing liquid into a device containing a liquid handling structure from a liquid storage arrangement (such as a blister pack) secured to the device overlapping an inlet port for admitting liquid into the device. The method comprises applying a pressure to the liquid storage arrangement to rupture the liquid storage arrangement and introduce liquid into the device. Then, the device is rotated to separate gas from the introduced liquid. Subsequently, the device is further rotated to cause liquid to flow through the liquid handling structure of the device.

In some embodiments, a method of delivering a volume of liquid to a fluid handling device operated by rotation comprises the steps of providing the fluid handling device with a communication port inlet and attaching a liquid storage package to the fluid handling device by a bonding layer extending outwards from the perimeter of the communication port inlet, the bonding layer defining a hole through its thickness of different contour of the communication port inlet, mechanically pressing a liquid storage package to promote rupture of the liquid storage package against the edge of the communication port inlet at least partially defined within the hole of the bonding layer, and rotating a cartridge to extract a liquid content from the liquid storage package to the fluid handling device to eliminate gas bubbles introduced on rupture.

In some aspects, the fluid handling device contains a receiving structure adjacent to the communication port to receive the liquid from the liquid storage package on rotation and subsequently dispensing the liquid to at least one adjacent structure.

In some aspects, the cartridge contains a receiving structure adjacent to the communication port to receive the liquid from the liquid storage package, the receiving structure containing at least one barrier preventing liquid flow to adjacent structures prior to rotation.

In some aspects, the fluid handling device contains a receiving structure to receive the liquid from the liquid storage package and is connected to adjacent structures by a siphon-like outlet conduit, to dispense the liquid to adjacent structures by rotation only after reaching a predefined volume.

In some aspects, the fluid handling device contains a receiving structure to receive the liquid from the liquid storage package and is connected to adjacent structures by a siphon-like conduit, to retain the liquid inside the receiving structure at a first rotational frequency and dispensing the liquid to adjacent structures at a subsequent step requiring at least one change to the first rotational frequency.

In some aspects, the receiving structure contains a second outlet from which liquid received from the liquid storage package on rotation escapes from the receiving structure, thereby leaving a metered volume in the receiving chamber prior to being dispensed to adjacent structures.

In some aspects, the predefined level is set to ensure that a minimum volume of liquid must enter the receiving structure in order to be dispensed to adjacent structures.

In some aspects, the fluid handling device contains a dispensing structure to receive the liquid from the liquid storage package and dispensing the liquid to adjacent structures, provided with an additional conduit connected to adjacent structures enabling the circulation of gas to maintain gas pressure in the system while the liquid is dispensed to adjacent structures.

In some aspects, the fluid handling device contains a receiving structure to receive the contents from the liquid storage package and dispensing the contents to adjacent structures configured with a spiral-like radially outermost aspect terminated in the outlet conduit from which liquid is dispensed.

Further described are analytical rotating cartridges comprising a sealed liquid storage package such as a blister pack attached to a fluid handling device containing a fluidic communication port designed such that the liquid storage package retains its sealing integrity during handling but when mechanically pressed ruptures in a predefined position of the contour the fluidic communication port inlet such that liquid content is admitted to the device and upon rotation flows from the liquid storage package into structures defined within the fluid handling device.

Disclosed embodiments relate to the liquid storage components, construction, positioning and operation of the cartridge, in order to enable the rupture of the blister pack when pressed, within a predefined range of mechanical force, so that it remains stable when stored and manipulated while easily ruptured when pressed by an operator or by automated means. Embodiments also relate to the configurations of the fluid handling device communication port inlet and adjacent fluidic structures for receiving the liquid from the liquid storage package on rupture in a controlled manner, and removing air bubbles generated on rupture via rotation of the device.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1A:
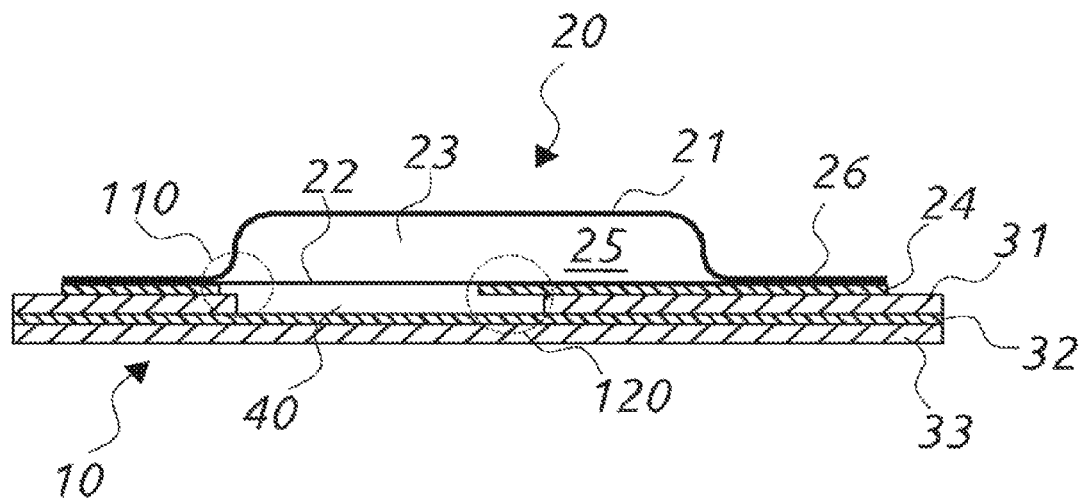
FIG. 1A illustrates a fluid handling device in cartridge format and including a liquid storage package in blister pack format.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

FIG. 1A illustrates a cartridge including a blister pack according to an embodiment. The cartridge 10 includes a blister pack 20 containing a liquid content 23. The blister pack is made from different materials, typically having an external material 21 that is sufficiently strong to minimize the risk of rupture from its surface both during storage and when liquid is released from the blister pack by application of mechanical pressure, as described below. This material may be an aluminum foil, cold form foil, plastic foil, or any type of deformable material capable to retain its shape without deteriorating mechanical and permeation properties.

For most applications demanding a long-time storage, it is preferable for the material 21 to be moisture-resistant and gas tight. The blister pack 20 is bonded to the cartridge 10 by a bonding material 24, and this material may be adhesive tape or acrylic glue, or any type of adhesive material or material capable of bonding parts by any treatment, namely light, temperature, pressure or time. A sealing material 22 is disposed between the external material 21 and the bonding material 24 and seals the blister pack 20. The external material 21 forms a storage chamber 25 and a flange 26 surrounding the storage chamber 25. The sealing material 22 is sealed to the flange 26 to seal the liquid 23 in the storage chamber 25. The sealing material 22 is sufficiently strong to maintain blister pack integrity but also sufficiently weak to be ruptured when the blister pack is pressed in a given range of applied mechanical forces.

In some embodiments the cartridge 10 is composed typically of three layers, a lower part 33, a bonding layer 32 and an upper part 31. These layers may have different functions, such as for example fluid, and liquid handling, optical or biological functions. However, other embodiments relate to devices having more or less than three layers, since the methods and mechanisms described will function for other constructions from single to multi-layered constructions. The cartridge may be of different thickness, in some embodiments below 10 mm, preferably below 2 mm.

Figure 1B:
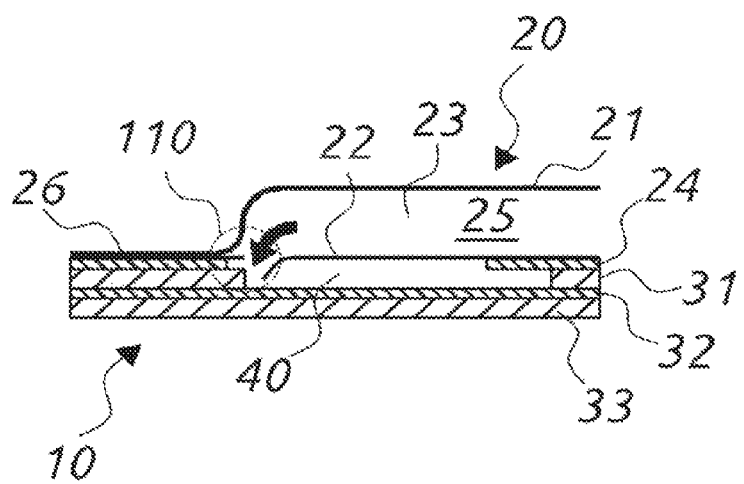
FIG. 1B illustrates further details of FIG. 1A.

FIG. 1B provides a detailed view of FIG. 1A. The cartridge is designed and constructed to promote rupture of the blister pack in a region 110. A cut-out region 40 is provided in the cartridge 10 below at least part of the blister pack 20 where the upper part 31 has a cut-out so that the blister pack is free-standing above the cut-out region 40, enabling sealing material 22 to tear or rupture against the contour or outer edge of the cut-out region 40 in a region 110 under the application of a mechanical force to the external material 21. It may be preferable, in many applications, to have the region 40 at a depth of below 1 mm.

The bonding material 24 defines an aperture through its thickness to allow for fluidic communication between the blister pack 20 and cartridge 10 upon rupture of the sealing material 22. The bonding material 24 extends outwards from the contour of the outer edge of region 40 to ensure sealing of the blister pack 20 to the cartridge 10. The outward extent of this bonding area depends of the bonding strength obtained by the materials and processes employed, and in particular on the mechanical force needed to rupture the blister pack.

In some embodiments, the contour of the aperture of the bonding material 24 is of a different pattern from the outer edge of the free-standing region 40. In some embodiments, the bonding material 24 extends inside the perimeter defined by the outer edge of the cut-out region 40 in a region 120 and outside the perimeter defined by the outer edge of the cut-out region 40 to expose an edge at the upper part 31 in a region 110. This arrangement favors the rupture of the sealing material 22 in the region 110, because a sharp edge of the upper part 31 is exposed in the region 110, while the bonding layer cushions this edge in the region 120. This arrangement thus can increase the reproducibility of a rupture location and thus of liquid extraction from the package. Additionally the contour of the aperture of the bonding material 24 can be adjusted, together with the liquid to gas ratio for the blister pack, to tune the range of mechanical forces required for rupturing the material.

Figure 1C:
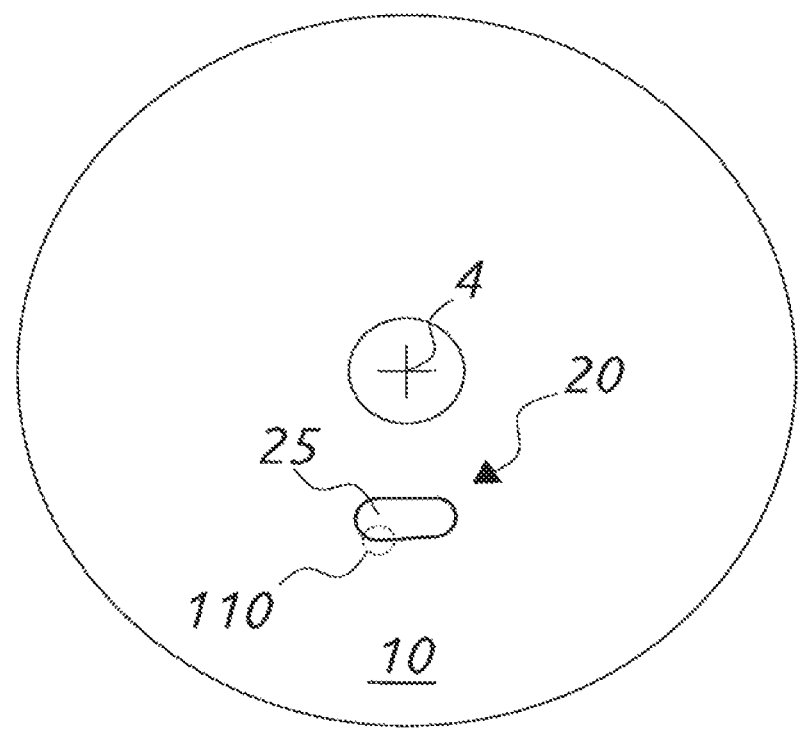
FIG. 1C illustrates a cartridge used for operation by rotation and including a liquid containing blister pack.

The cartridge described above with reference to FIG. 1A and FIG. 1B can thus be operated without the introduction of additional rupturing parts and therefore be of simple implementation and easy to manufacture. In particular, in the case of analytical devices operated by rotation about an axis 4, as illustrated in FIG. 1C (omitting the flange 26 of the blister pack 20 for clarity of illustration), it can be advantageous to position the favored rupture region 110 at an outermost radial aspect of the blister pack 20, specifically an outermost radial aspect of the storage chamber 25, to prevent the entrapment of residual liquid contained in the storage chamber 25 after rupture and therefore favor emptying of all liquid in the blister pack 20.

The shape of the cut-out region 40, in particular the contour of the outer edge against which material 22 ruptures is an important consideration for reproducible blister pack rupture and liquid admission to the cartridge. This will now be discussed in detail with reference to FIGS. 2A-C.

Figure 2A:
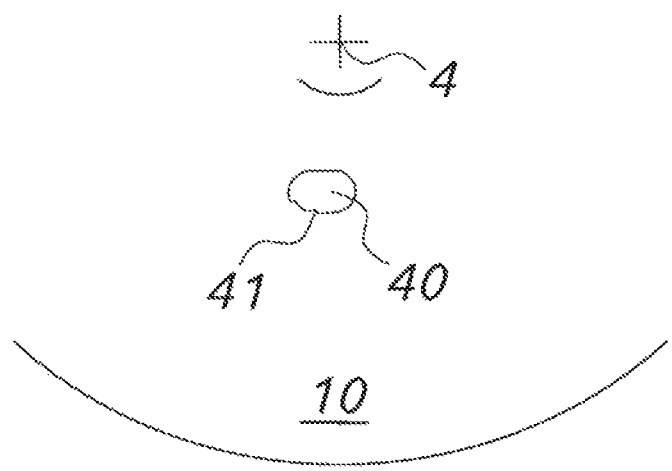
FIG. 2A illustrates a portion of a cartridge having a fluid communication port defining a contour adapted for blister pack rupture and liquid dispensing.
Figure 2B:
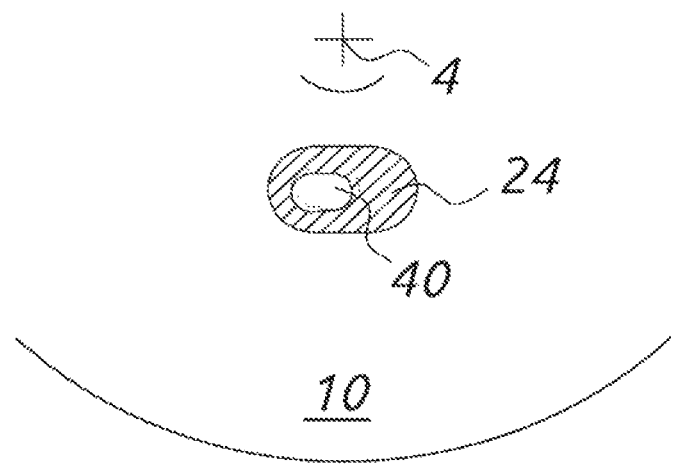
FIG. 2B illustrates a portion of the cartridge of FIG. 2A together with a bonding layer for a liquid containing blister pack.
Figure 2C:
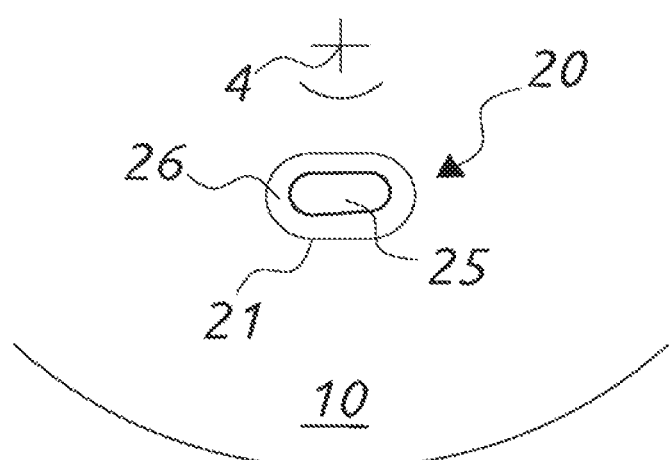
FIG. 2C illustrates a top view of the cartridge of FIGS. 2A and 2B having a liquid containing blister pack bonded to the bonding layer.

FIGS. 2A-C illustrate a portion of the cartridge 10 according to an embodiment, having a cut-out region 40 designed to facilitate reproducible blister pack rupture and liquid dispensing. When the cut-out region 40 is too small, the blister pack rupture will only occur with very high mechanical forces, and therefore not be of practical use in many applications. The same applies when the region 40 is too large, because in this case the blister pack materials 21 and 22 will tend to accommodate the applied mechanical force by shape change and by elastic deformation without localized rupture. This latter effect is of increasing significance as the depth of the cut-out region 40 decreases. So, in particular for applications having cartridges of less than 2 mm thickness, and a chosen height beneath the cut-out region 40 of less than 1 mm, it is advantageous to provide additional features to favor reproducible blister pack 20 rupture onset.

FIGS. 2A and 2B illustrate a part of the cartridge and a blister pack according to an embodiment. The cartridge 10 is used for operation by rotation about an axis of rotation 4 and contains a cut-out region 40 having a non-regular contour shape to facilitate localized rupture of the blister pack 20. In particular the cut-out is non-regularly shaped to provide spikes 41 extending inwards, level with an external surface at the cartridge 10, specifically upper part 31. The bonding material 24 is placed on the external surface to have a portion of the bonding material 24 disposed inside the perimeter defined by the contour of the cut-out region 40 so that the blister pack 20 does not rupture in that region as described with reference to region 120 above. The non-regular contour shape is provided in the region 110 described above, thus further facilitating rupture.

FIG. 2C illustrates a top view of the cartridge with the blister pack 20 in place on top of the bonding material 24. The size and shape of the blister pack 20 may, in some applications, be optimized to be manually pressed. The geometry, dimensions, and orientation of the different elements, cut-out region 40, bonding material 24 and blister pack 20 can be optimized to retain integrity when stored and manipulated whilst being easily ruptured when mechanically pressed by an operator or by automated means.

Naturally, the above considerations discussed with reference to FIGS. 2A-C apply equally to non-rotational embodiments, where liquid propulsion mechanisms other than a centrifugal force are applied.

Figure 3A:
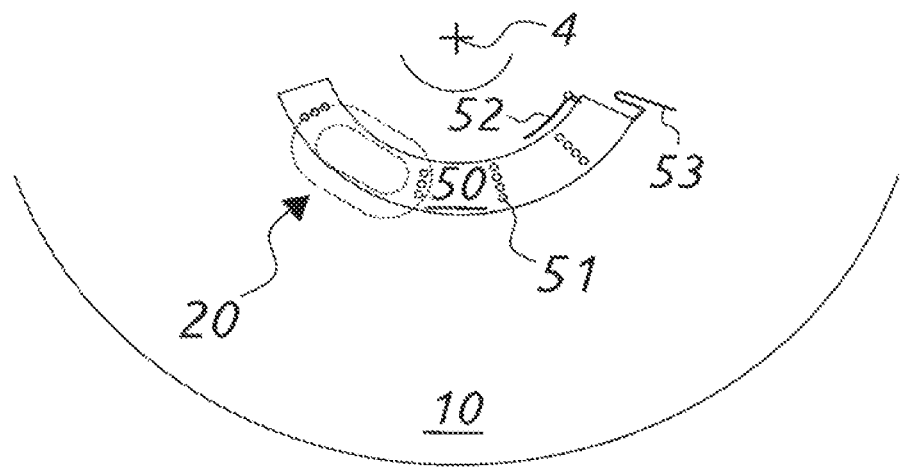
FIG. 3A illustrates a portion of a cartridge having fluidic structures adapted for blister pack rupture and liquid handling functions for analytical procedures.

FIG. 3A illustrates a part of a cartridge and a liquid blister pack 20 according to an embodiment, the cartridge having fluidic structures and communication ports arranged to facilitate blister pack rupture, liquid dispensing and analytical performance. For the purpose of illustration, the cartridge is depicted with an outer layer removed to reveal underlying structures and the position of the blister pack 20 on the removed layer relative to the underlying structures is illustrated by a dashed outline.

The cartridge 10 is operated by rotation about an axis 4. The blister pack 20 is bonded to the cartridge 10 as described above, overlapping the cut-out region 40 (not visible in FIG. 3A). A liquid receiving structure 50, optimized for liquid handling functions is provided in the region of the cut-out region 40 to receive liquid from the blister pack 20. (The cartridge 10 may be used in many, different applications, in particular analytical devices and systems.)

A liquid outlet 53 is connected to an outlet port of the liquid receiving structure 50 to allow liquid to flow from the liquid receiving structure 50 to downstream liquid handling structures. Further, a vent conduit 52 is provided to connect the liquid receiving structure 50 to atmospheric pressure or a gas conduit system for equalizing pressure around the cartridge 10.

The outlet 53 may be configured as a capillary siphon to block liquid flow under rotation as long as capillary action does not draw liquid into the outlet sufficiently for further rotation to cause liquid to be siphoned from the liquid receiving structure 50. To this end, the radially inner most aspect of the outlet 53, e.g. the crest of the siphon bend, is disposed radially inwards of the liquid level in the receiving structure 50 after the liquid 23 has been compacted by rotation. This level is determined by the amount of liquid held by the blister pack 20 and the geometry and dimension of the receiving structure 50.

Alternatively, the outlet may be arranged as a siphon which primes when a liquid level in the chamber 50 exceeds a level corresponding to the radially innermost point of the outlet 53. This can be achieved by disposing the radially innermost aspect of the outlet 53 radially outward from the liquid level after the liquid 23 has been compacted.

The liquid receiving structure 50 in some embodiments may be contained in the upper part 31 of the cartridge 10, for example having a thickness below 10 mm, preferably below 1 mm. Equally the liquid receiving structure or chamber 50 may be defined by one or more of parts 31, 32 and 33 individually or in co-operation. The liquid receiving structure 50 may contain physical barriers such as posts or pillars 51 for a dual purpose:
(i) maintaining the structural integrity of the liquid receiving structure 50 when the cartridge 10 is manipulated and when the blister pack 20 is mechanically pressed;
(ii) minimize the risk of liquid admitted to the liquid receiving structure 50 on rupture to flow into adjacent structures before this is desirable, e.g. prior to rotation.

The second purpose can be of paramount importance for many applications in which the cartridge 10 contains a plurality of fluidic structures operated by rotation, and where capillary effects play a significant role. In particular, when blister pack 20 is pressed and ruptured, then at least part of the liquid content 23 will move into the receiving structure 50. Due to the mechanical force applied and gas contained in the blister pack, the liquid content 23 admitted to the receiving structure 50 may contain gas bubbles which may compromise subsequent cartridge operation. Additionally, if part of liquid 23 admitted to the receiving structure 50 reaches the outlet 53 prior to rotation then the liquid may also flow by capillary action prior to an initial phase of rotation, compromising the liquid functions for which the cartridge was designed.

Further, many applications and devices require the use of closed circuits, for both liquid and gas flow. This fact is relevant for applications of blood analysis or other processing or analytical applications where contamination from or to the sample may be undesirable. In such circumstances, gas displacement during liquid flow can be critical for proper operation of the device to avoid gas pressure variations which will also affect the flow of the liquid. For example, in some embodiments the liquid receiving structure 50 is provided with the vent conduit 52 connecting to adjacent structures where liquid 23 will flow, to avoid gas pressure variations in the device while it is being operated. This would be compromised if the vent conduit 52 would be blocked by a liquid plug.

Therefore, barriers to liquid flow such as pillars 51 are provided in the liquid receiving structure to prevent liquid advancing from the blister pack into the outlet 53 prior to initial rotation and to prevent liquid ingress into the vent conduit 52 by limiting uncontrolled liquid flow prior to rotation. In one specific embodiment, as illustrated in FIGS. 3A-3D, an array of pillars 51 in the form of several spaced rows is provided in the liquid receiving structure 50.

Operation of the device is now described with reference to FIGS. 3B-3D.

Figure 3B:
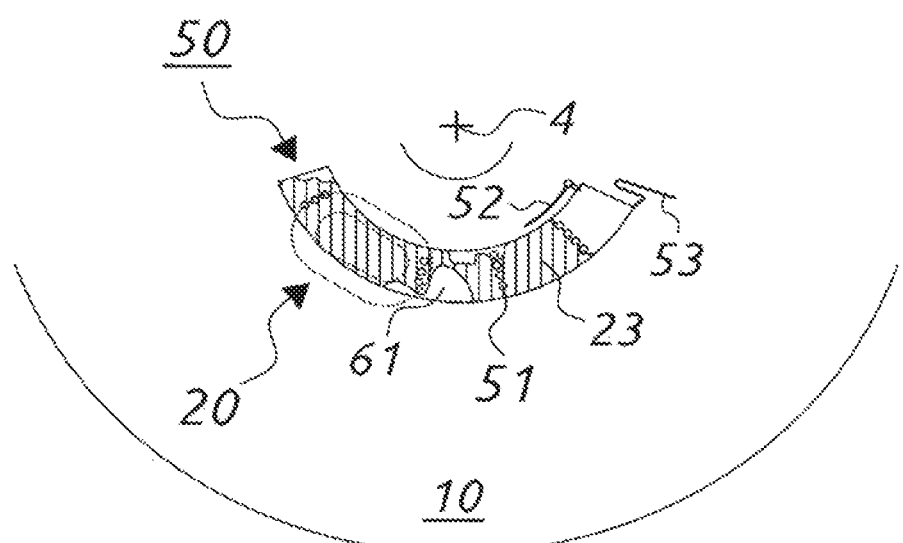
FIGS. 3B-3D illustrate the operation of the cartridge of FIG. 3A.

FIG. 3B illustrates a state after rupturing the blister pack and prior to rotation. The blister pack 20 has been mechanically pressed and has ruptured. Liquid 23 fills part of the receiving structure 50, along with gas 61 released from the blister pack on rupture. The pillars 51 prevent liquid from reaching the outlet 53 and vent conduit 52.

Figure 3C:
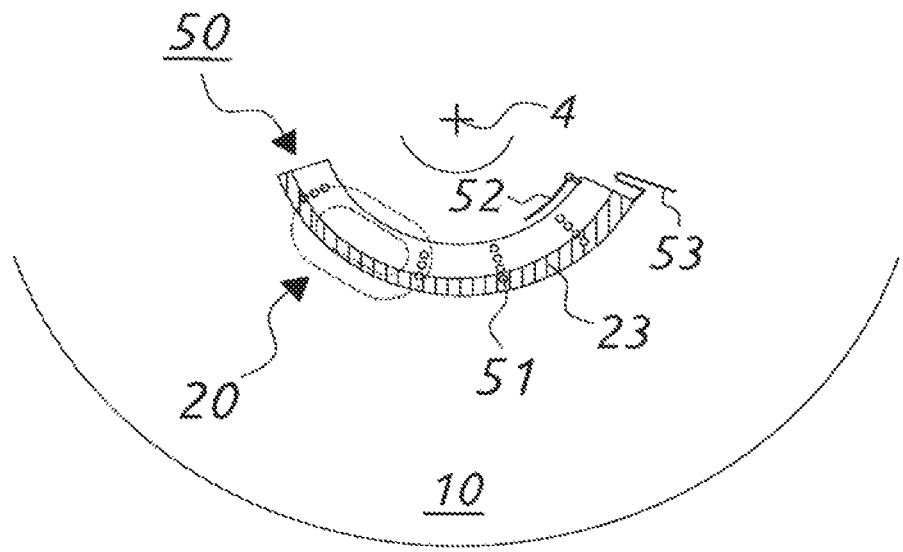

FIG. 3C illustrates a state during an initial phase of rotation. The liquid 23 is driven towards the outermost radial aspects of the receiving structure 50 by the action of the centrifugal force, and as a result gas 61 moves inwards leaving a compact of the liquid 23 in the receiving structure 50. Liquid retained in the blister pack after rupture will also flow into receiving structure 50 by the action of the centrifugal force provided that the fluidic communication induced on rupture is radially beyond the liquid position inside the blister pack. In some embodiments, liquid dispensing to adjacent structures and downstream circuits is delayed for a sufficient amount of time so that the gas 61 is removed from the liquid content 23, by forming the liquid compact 62 against the outermost radial aspects of the receiving structure 50. In some embodiments, this may be achieved as described above by designing the outlet 53 with a portion of its length radially inwards from the outlet port of the receiving structure 50, followed by another portion extending radially outwards from the innermost radial position of the outlet. In some embodiments, the outlet 53 is designed such that a minimum amount of liquid 23 must be admitted to the receiving chamber 50 or otherwise liquid will not be dispensed to further structures. These embodiments are useful, for example, to control the liquid content of the blister, or efficiency of the rupture mechanism and to eventually discard devices in which a minimum amount of liquid required for adequate operation of the device has not been received from the blister pack 20.

As described above, the outlet 53 has, in some embodiments, a siphon-like shape, in order to retain the liquid 23 in the receiving structure 50 until a pre-defined liquid volume has been admitted to the chamber. Alternatively, in some embodiments this channel may be arranged as a capillary siphon in which all liquid admitted from the blister pack 20 is retained in the receiving chamber 50 at a first rotational frequency for any desired period of time. After this period, liquid may be dispensed to adjacent structures after at least one change in rotational frequency, to enable the liquid to advance into the outlet 53 by capillary action and then dispensing the liquid at this or another rotational frequency. In other embodiments, also using the capillary siphon outlet arrangement described above, the receiving structure 50 contains a second outlet from which liquid in excess of a predefined volume escapes from structure 50 during a first rotation, to then dispense a metered liquid volume at subsequent steps. The use of well defined, or metered, liquid volumes can be of critical importance to many analytical procedures as, for example, dilution ratios and concentrations are dependent on liquid volumes.

Figure 3D:
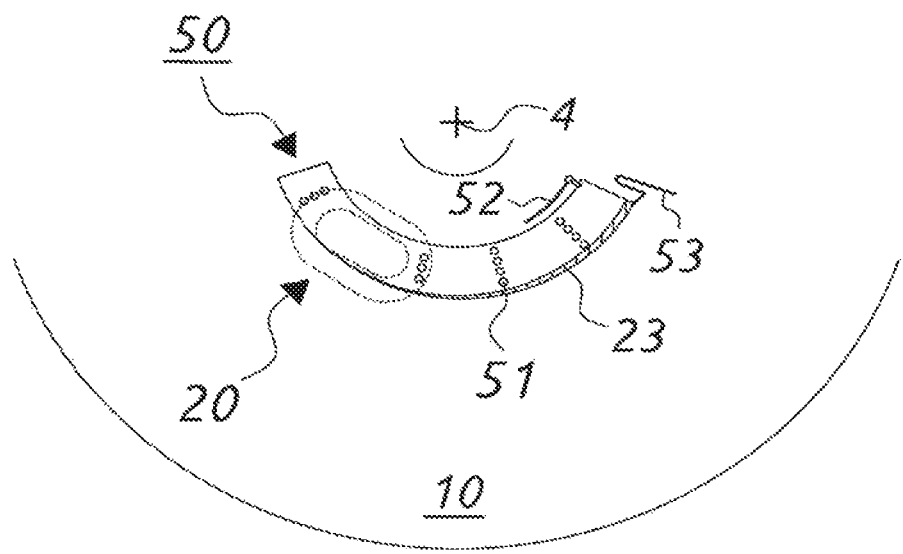

FIG. 3D illustrates a state during further rotation and liquid dispensing. When the liquid 23 reaches a certain level defined by the innermost radial position of the outlet conduit 53, the liquid 23 will start to flow to adjacent downstream structures (alternatively, the start of liquid flow through the outlet 53 can be controlled by the rotational frequency, as described above). The receiving structure 50 is, in some embodiments, shaped to minimize the amount of liquid that remains entrapped in its volume. In particular, the outermost radial aspect of the receiving structure 50, along its angular extent, increases in radial extent towards the outlet port where outlet 53 starts, such as for example having an outermost perimeter following a spiral locus.

As described above, the vent conduit 52 ensures a gas pressure equilibrium within the cartridge 10 and therefore prevents liquid flow being affected by gas pressure variations. The vent port of the liquid receiving structure 50 where vent conduit 52 starts, is disposed in a radially inward aspect of the liquid receiving chamber 50 to reduce the risk of blocking the vent conduit 52 by the presence of liquid upon rupture and subsequent rotation of the device.

It can be noted that, by placing the vent conduit 52 radially inward of the outlet port, the risk of clogging is reduced by liquid being driven radially outward during rotation. This can help to maintain pressure equilibration.

After liquid dispensing from the blister pack into adjacent downstream structures has occurred via the liquid receiving structure 50 the liquid receiving structure 50 is again in an empty state as illustrated in FIG. 3A. The device 10 may then be operated according to subsequent, application specific, liquid handling functions.

In some embodiments the receiving structure 50 may also provide additional functions, such as aliquoting functions. For this purpose, a cartridge 10 may have a liquid receiving structure 50 with a multitude of outlets 53, placed in such a way that multiple liquid volumes are dispensed from the liquid blister pack 20 into different downstream structures. Additionally, solid reagents may be incorporated in the receiving structure 50 which are re-suspended the moment liquid is admitted to the structure until no liquid remains. Embodiments may have more than one liquid storage package incorporating different liquid reagents and bonded to a single cartridge. These may be ruptured simultaneously or at different stages of the analytical procedure (or rotation protocol), or even allow for rupturing of only those packages which are required for a particular procedure, thus enabling the use of identical cartridges for applications requiring different reagents.

The above description of embodiments is made by way of illustration and not for the purpose of limitation. In particular, the above description, being made in terms of a "blister pack", is not so limited and equally applies to any other suitable liquid storage arrangement from which liquid can be released by mechanical pressure. Many alterations, modifications and juxtapositions of the features described above will occur to the person skilled in the art and form part of the invention.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of introducing a liquid into a fluid handling device comprising a liquid handling structure from a liquid storage arrangement secured to the fluid handling device overlapping an inlet port for admitting the liquid into the fluid handling device, and a cartridge containing a receiving structure adjacent to the inlet port to receive the liquid from the liquid storage arrangement, wherein the receiving structure contains at least one barrier providing a resistance to liquid flow to adjacent structures prior to rotation, and the at least one barrier comprises a support structure disposed within the receiving structure to increase the structural strength of a wall between an external surface of the liquid handling device and the receiving structure, the method comprising:

applying a pressure to the liquid storage arrangement to rupture the liquid storage arrangement and introduce the liquid into the fluid handling device;

rotating the fluid handling device to separate a gas from the introduced liquid; and subsequently rotating the fluid handling device to cause the liquid to flow through the liquid handling structures of the fluid handling device.

2. The method of claim 1, wherein the fluid handling device further comprising a communication port inlet and a liquid storage arrangement attached to the fluid handling device by a bonding layer extending outwards from the perimeter of the communication port inlet, the bonding layer defining a hole through a thickness of the bonding layer of different contour of the communication port inlet, and wherein rotating the fluid handling device to separate gas from the introduced liquid comprises mechanically pressing a liquid storage arrangement to promote rupture of the liquid storage arrangement against the edge of the communication port inlet at least partially defined within the hole of the bonding layer, and rotating a cartridge to extract a liquid content from the liquid storage arrangement to the fluid handling device to eliminate gas bubbles introduced on rupture.

3. The method of claim 2, wherein the cartridge contains a receiving structure adjacent to the communication port to receive the liquid from the liquid storage arrangement, the receiving structure containing at least one barrier providing a resistance to liquid flow to adjacent structures prior to rotation.

4. The method of claim 1, wherein the fluid handling device contains a receiving structure to receive the liquid from the liquid storage arrangement and is connected to adjacent structures by an outlet conduit comprising a siphon, to dispense the liquid to adjacent structures by rotation only after reaching a predefined volume.

5. The method of claim 1, wherein the fluid handling device contains a receiving structure adjacent to the inlet port to receive the liquid from the liquid storage arrangement on rotation and subsequently dispensing the liquid to at least one adjacent structure.

6. The method of claim 1, wherein the fluid handling device contains a receiving structure to receive the liquid from the liquid storage arrangement and is connected to adjacent structures by a conduit comprising a siphon, to retain the liquid inside the receiving structure at a first rotational frequency and dispensing the liquid to adjacent structures at a subsequent step requiring at least one change to the first rotational frequency.

7. The method of claim 6, wherein the receiving structure contains a second outlet from which liquid received from the liquid storage arrangement on rotation escapes from the receiving structure, thereby leaving a metered volume in the receiving chamber prior to being dispensed to adjacent structures.

8. The method of claim 1, wherein a predefined level is set to ensure that a minimum volume of liquid must enter the receiving structure in order to be dispensed to adjacent structures.

9. The method of claim 1, wherein the fluid handling device contains a dispensing structure to receive the liquid from the liquid storage arrangement and dispensing the liquid to adjacent structures, provided with an additional conduit connected to adjacent structures enabling the circulation of gas to maintain gas pressure in the system while the liquid is dispensed to adjacent structures.

10. The method of claim 1, wherein the fluid handling device contains a receiving structure to receive the contents from the liquid storage arrangement and dispensing the contents to adjacent structures configured with a radially outermost aspect comprising a spiral and terminated in an outlet conduit from which liquid is dispensed.

11. The method of claim 1, wherein the fluid handling device contains a receiving structure to receive the liquid from the liquid storage arrangement and dispensing the liquid to adjacent structures, provided with an additional conduit connected to adjacent structures enabling the circulation of gas to maintain gas pressure in the system while the liquid is dispensed to adjacent structures.

12. The method of claim 1, wherein the fluid handling device contains a dispensing structure to dispense the contents from the liquid storage arrangement and dispensing the contents to adjacent structures configured with a radially outermost aspect comprising a spiral and terminated in an outlet conduit from which liquid is dispensed.

13. The method of claim 1, wherein the fluid handling device contains a receiving structure to receive the liquid from the liquid storage arrangement, and wherein once the liquid from the liquid storage arrangement is received in the receiving structure, the liquid is capable of being dispensed to adjacent structures, provided with an additional conduit connected to adjacent structures enabling the circulation of gas to maintain gas pressure in the system while the liquid is dispensed to adjacent structures.

14. The method of claim 13, wherein the fluid handling device contains a receiving structure to receive the liquid from the liquid storage arrangement, and wherein the receiving structure is capable of dispensing the liquid received from the liquid storage arrangement to adjacent structures configured with a radially outermost aspect comprising a spiral and terminated in an outlet conduit from which liquid is dispensed.

* * * * *